United States Patent [19]
Nguyen et al.

[11] Patent Number: 5,958,963
[45] Date of Patent: Sep. 28, 1999

[54] APHICIDAL PYRAZOLES

[75] Inventors: Dang Long Nguyen, Hochiminville, Viet Nam; Robin Keith Jones, Pretoria, South Africa

[73] Assignee: Rhone-Poulenc Agrochimie, Lyon, France

[21] Appl. No.: 08/811,029

[22] Filed: Mar. 4, 1997

[30] Foreign Application Priority Data

Mar. 4, 1996 [FR] France ................................. 96 02987
Jul. 2, 1996 [FR] France ................................. 96 08488

[51] Int. Cl.⁶ ...................... A61K 31/415; C07D 231/44
[52] U.S. Cl. ........................ 514/404; 514/407; 548/367.4
[58] Field of Search ..................... 514/404; 548/367.4

[56] References Cited

U.S. PATENT DOCUMENTS

| | | | |
|---|---|---|---|
| 5,232,940 | 8/1993 | Hatton et al. ........................... | 514/407 |
| 5,270,043 | 12/1993 | Twinn et al. ......................... | 514/404 X |
| 5,306,694 | 4/1994 | Phillips et al. ........................ | 504/253 |
| 5,321,040 | 6/1994 | Huang et al. ......................... | 514/407 |
| 5,506,254 | 4/1996 | Kirstgen et al. ....................... | 514/406 |
| 5,580,843 | 12/1996 | Stetter et al. ....................... | 514/404 X |
| 5,608,077 | 3/1997 | Hatton et al. .................... | 548/367.4 X |
| 5,614,182 | 3/1997 | Davidson et al. ......................... | 424/84 |
| 5,637,607 | 6/1997 | Pilato et al. ............................ | 514/404 |
| 5,696,144 | 12/1997 | Royalty et al. ......................... | 514/404 |

FOREIGN PATENT DOCUMENTS

| | | |
|---|---|---|
| 0295117 | 12/1988 | European Pat. Off. . |
| 0500209 | 8/1992 | European Pat. Off. . |
| 0691332 | 1/1996 | European Pat. Off. . |
| 19511269 | 10/1995 | Germany . |
| 96/25401 | 8/1996 | WIPO . |

OTHER PUBLICATIONS

Database CAPLUS on STN®, Chemical Abstracts Service, (Columbus, Ohio), Accession No. 1994:624264, Burris E. et al., Proc.—Beltwide Cotton Conf. 2, 838–844 (1994), abstract.

Burris et al, Proc.–Beltwide Cotton Conf. 2, 838–844 (1994).

Mayer et al, Arthropod Management Tests, vol. 20, 30 (1995).

Kern, *Arthropod Management Tests*, vol. 21, No. 0, pp. 71–72 (1996).

Mayer et al, Database Cropu, STN–accession No. 95–88542 (1995).

Colliot et al, Database Cropu, STN accession No. 93–82326 (1993).

Colliot et al, "Fipronil: A New Soil and Foliar Broad Spectrum Insecticide" in Prot. Conf. Pest. Dis. 1992, vol. 1, pp. 29–34 (Brighton Crop Protection Conference, Nov. 23–25, 1992).

Singh et al, *Chemical Abstracts*, vol. 86, No. 19, May 9, 1997, abstract No. 134847.

Matsumoto et al, *Chemical Abstracts*, vol. 90, No. 19, May 7, 1979, abstract No. 146988.

*Primary Examiner*—Michael G. Ambrose
*Attorney, Agent, or Firm*—Burns, Doane, Swecker & Mathis, L.L.P.

[57] ABSTRACT

Method for the protection of citrus crops against attacks by greenfly of the Toxoptera type, which comprises treating the crops or the medium in which they grow with a 1-phenylpyrazole or 1-(2-pyridyl)pyrazole compound.

20 Claims, No Drawings

APHICIDAL PYRAZOLES

BACKGROUND OF THE INVENTION

1. Field of the Invention

The present invention relates to a method for the treatment of plants against attacks by certain greenfly.

2. Description of the Related Art

Various 1-phenylpyrazoles and 1-(2-pyridyl)pyrazoles are known as insecticides. For example, International Patent Publication No. WO 87/03781 and European Patent Publication No. 0295117 describe insecticidal 1-(substituted phenyl)pyrazoles. Also, International Patent Publications No. WO 93/06089 and WO 94/21606 describe insecticidal 1-(4-SF$_5$ substituted phenyl)heterocycles which may be pyrroles or imidazoles or pyrazoles.

OBJECTS AND SUMMARY OF THE INVENTION

A first object of the invention is to combat, curatively or preventatively, attacks of plants by certain greenfly.

Another object of the present invention is to protect plants against diseases due to attacks by greenfly of the Toxoptera genus.

Another object of the present invention is to protect plants, such as trees, which bear citrus fruit.

Another object of the present invention is to provide new aphicides.

Another object of the present invention is to protect plants bearing citrus fruit against attacks by greenfly of the Toxoptera type.

It has now been found that these aims can be achieved in whole or in part by virtue of the method of the invention.

The present invention accordingly provides a method for the protection of crops, for example citrus trees, against attack by greenfly of the Toxoptera genus which comprises treating the crops or the medium in which they grow with an insecticidally active material of the 1-phenylpyrazole or 1-(2-pyridyl)pyrazole type, in an amount effective to protect said crops against said attack.

The method according to the invention is noteworthy because of the high level of effectiveness of compounds of formula (I) against Toxoptera spp., an effectiveness which is much greater than that with respect to other greenfly.

The 1-phenylpyrazoles and 1-(2-pyridyl)pyrazoles capable of being used in the invention are advantageously compounds of formula (I):

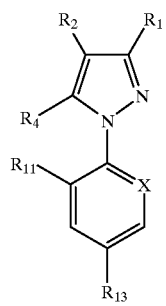

(I)

in which:

$R_1$ is CN or methyl;

$R_2$ is $S(O)_nR_3$;

$R_3$ is alkyl or haloalkyl;

$R_4$ represents a hydrogen or halogen atom or an $NR_5R_6$, $S(O)_mR_7$, $C(O)R_7$, $C(O)O$—$R_7$, alkyl, haloalkyl, $OR_8$ or —N=C($R_9$)($R_{10}$) radical;

$R_5$ and $R_6$ each independently represent the hydrogen atom or an alkyl, haloalkyl, C(O)alkyl or $S(O)_rCF_3$ radical, or $R_5$ and $R_6$ together form a divalent alkylene radical which is optionally interrupted by one or two divalent heteroatoms, such as oxygen or sulfur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl radical optionally having one or more substituents selected from the group consisting of halogen, OH, —O-alkyl, —S-alkyl, cyano and alkyl;

X represents a trivalent nitrogen atom or a C—$R_{12}$ radical, the other three valencies of the carbon atom forming part of the aromatic ring;

$R_{11}$ and $R_{12}$ each represent, independently of each other, a hydrogen or halogen atom;

$R_{13}$ represents a halogen atom or a haloalkyl, haloalkoxy, $S(O)_qCF_3$ or $SF_5$ group; and m, n, q and r each represent, independently of one another, an integer equal to 0, 1 or 2;

with the proviso that, when $R_1$ is methyl, then $R_3$ is haloalkyl, $R_4$ is $NH_2$, $R_{11}$ is Cl, $R_{13}$ is $CF_3$ and X is N.

DETAILED DESCRIPTION OF THE INVENTION AND PREFERRED EMBODIMENTS

The alkyl radicals in the definition of formula (I) generally contain from 1 to 6 carbon atoms.

When $R_5$ and $R_6$ together with the nitrogen atom to which they are attached form a ring, the ring is generally 5- or 6-membered.

A preferred class of compounds of formula (I) is composed of the compounds such that $R_1$ is CN and/or $R_3$ is haloalkyl and/or $R_4$ is $NH_2$ and/or $R_{11}$ is a halogen atom and/or $R_{12}$ is a halogen atom and/or $R_{13}$ is haloalkyl.

When $R_{10}$ is a heteroaryl radical, it has 5 or 6 ring atoms, 1 to 3 of which are heteroatoms selected from the group consisting of O, S and N. Illustrative heteroaryl radicals are pyridyl, thienyl, furanyl and pyrrolyl.

A compound of formula (I) which is very particularly preferred in the invention is 1-[2,6-Cl$_2$-4-CF$_3$phenyl]-3-CN-4-[SO-CF$_3$]-5-NH$_2$pyrazole, i.e. 5amino-3-cyano-1-(2,6-dichloro-4-trifluoromethyl)phenyl-4-trifluoromethylsulfinylpyrazole, hereinafter known as Compound A.

Compounds of formula (I) can be prepared according to one or other of the processes described in International Patent Publications No. WO 87/03781, 93/06089 or 94/21606 or European Patent Publication No. 0295117, or any other process coming within the competence of the person skilled in the art of chemical synthesis.

Formulations which can be used in the invention are described in particular in International Patent Publications No. WO 87/03781, 93/06089 and 94/21606 and in European Patent Publication No. 0295117. The formulations described in the prior art can be adapted in order to make them still more suitable for specific use herein depending on the local conditions, in particular by additions of appropriate adjuvants.

The 1-arylpyrazoles used in the present invention, that is, the 1-phenylpyrazoles and 1-(2-pyridyl)pyrazoles of formula (I), can advantageously be formulated as fluid or liquid compositions, wettable powders or microemulsions. Such formulations generally comprises one or a number of inert vehicles or diluents which are solid or liquid and which are agronomically acceptable in the case of application to cultivated areas.

Formulations which are suitable for the implementation of the method according to the invention generally comprise from about 0.0001 to about 95% by weight of active material of formula (I). As regards concentrated formulations for commercial use (for storage, sale or transportation), same advantageously comprise from about 0.1 to about 15% by weight of active material. The compositions as used by the applicator are generally much more dilute compositions. In addition to the active material, the compositions according to the invention may contain various vehicles, which are solid or liquid, surfactants and other adjuvants of the most varied natures but which are agronomically acceptable.

Wettable powder or concentrated granule formulations can be prepared by milling a 1-arylpyrazole of formula (I) with approximately 1% to approximately 20% by weight of solid anionic surfactant. One suitable anionic surfactant is the dioctyl ester of the sodium salt of sulfosuccinic acid. Approximately 85% to approximately 95%, by weight, of inert diluent, such as montmorillonite, attapulgite, chalk, talc, kaolin, diatomaceous earth, pumice, silicates or other similar products, can be included in such formulations, as well as the other adjuvants indicated above.

In addition to the granules and wettable powders described above, use may also be made of fluid formulations, and in particular of formulations which are readily dispersible in water, in order to facilitate their dispersion on the site of application, in particular in agriculture.

The pyrazoles used in the present invention have a low solubility but can be used at low doses. It is therefore possible to employ them in solutions or emulsions or, preferably, in the form of aqueous or non-aqueous suspensions comprising the appropriate adjuvants and/or cosolvents. Acetone and methyl ethyl ketone can be used as cosolvents. Any liquid medium can be used, provided that it is toxic neither to the plants nor to the environment. When the active material has little solubility, use may be made of cosolvents and/or of wetting or dispersing agents. Other additives can also be employed, such as talc. The active materials of formula (I) can be absorbed on vehicles, for example vermiculite, clay, talc, kaolin or others, in particular in order to form granules.

The 1-arylpyrazoles of the invention are advantageously employed in leaf or soil treatment, preferably leaf treatment. At a practical level, the doses applied on the surface to be treated are generally from about 5 to about 800 g/ha, preferably from about 25 to about 400 g/ha and more preferentially still from about 50 to about 100 g/ha. Higher doses are preferred for large trees. Lower doses are suitable for small trees.

The products according to the invention are applied preventatively or curatively. For the purpose of economy, it is generally preferred to employ the products according to the invention curatively, more particularly on the appearance of the first greenfly of the Toxoptera genus.

The crops for which the invention is applicable comprise in particular citrus crops, especially orange, lemon, mandarin, clementine and grapefruit crops.

The following examples, given without implied limitation, illustrate the invention and show how it can be implemented.

Example 1

Orange trees were treated at the time of the appearance of an attack by greenfly of the Toxoptera genus. The application was carried out in the form of an aqueous dispersion/solution containing 3 g per hectoliter of Compound A, which corresponds to the application of 60 g/ha of this active material.

After 3 days, 90% of the greenfly are observed to have disappeared in comparison with untreated trees.

Example 2

Example 1 was repeated, using an aqueous dispersion/solution containing 5 g per hectoliter of Compound A, which corresponds to the application of 100 g/ha of this active material.

After 3 days, 95% effectiveness against Toxoptera spp. is observed, in comparison with untreated trees.

Example 3

Example 1 was repeated in the case where the attack by the greenfly is due to the species Toxoptera aurantii and while using an aqueous dispersion/solution containing 10 g per hectoliter of Compound A, which corresponds to the application of 200 g/ha of this active material.

After 14 days, 80% effectiveness is observed, in comparison with untreated trees.

Example 4

Example 3 was repeated, using an aqueous dispersion/solution containing 20 g per hectoliter of Compound A, which corresponds to the application of 400 g/ha of this active material.

After 14 days, 90% effectiveness is observed, in comparison with untreated trees.

Example 5

Example 1 was repeated in the case where the attack by the greenfly is due to the species *Toxoptera citricidus*. The same results are obtained.

Example 6

Example 2 was repeated in the case where the attack by the greenfly is due to the species *Toxoptera citricidus*. The same results are obtained.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for treating a citrus plant in need of protection against attack by greenfly of the Toxoptera genus, said method comprising applying to said citrus plant or to the medium in which it grows, in an amount effective to protect said citrus plant against said attack, a compound having the formula:

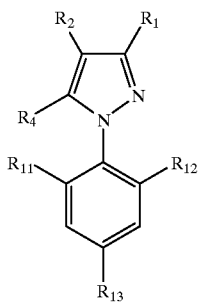

(I)

wherein:

$R_1$ is CN;

$R_2$ is $S(O)_n R_3$;

$R_3$ is $C_1-C_6$ haloalkyl;

$R_4$ is $NH_2$;

$R_{11}$ is halogen;

$R_{12}$ is halogen;

$R_{13}$ is $C_1-C_6$ haloalkyl; and n is an integer equal to 0, 1 or 2.

2. A method according to claim 1, wherein the citrus crop is an orange, lemon, mandarin, clementine or grapefruit crop.

3. A method according to claim 1, wherein the compound of formula (I) is applied to the leaves or to the soil.

4. A method according to claim 1, wherein the compound of formula (I) is applied at a rate of from about 5 to about 800 g/ha.

5. A method according to claim 1, wherein the compound of formula (I) is applied at a rate of from about 25 to about 400 g/ha.

6. A method according to claim 1, wherein the compound of formula (I) is applied at a rate of from about 50 to about 100 g/ha.

7. A method for treating a citrus plant in need of protection against attack by greenfly of the Toxoptera genus, said method comprising applying to said citrus plant or to the medium in which it grows, in an amount effective to protect said citrus plant against said attack, the compound 5-amino-3-cyano-1-(2,6-dichloro-4-trifluoromethyl)phenyl-4-trifluoromethylsulfinylpyrazole.

8. A method for treating a citrus plant attacked by greenfly of the Toxoptera genus, said method comprising applying to said citrus plant or to the medium in which it grows, in an amount effective to kill said greenfly, a compound of the formula:

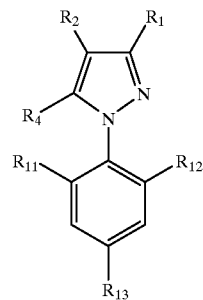

(I)

wherein:

$R_1$ is CN;

$R_2$ is $S(O)_n R_3$;

$R_3$ is $C_1-C_6$ haloalkyl;

$R_4$ is $NH_2$;

$R_{11}$ is halogen;

$R_{12}$ is halogen;

$R_{13}$ is $C_1-C_6$ haloalkyl; and n is an integer equal to 0, 1 or 2.

9. A method according to claim 7, wherein the citrus crop is an orange, lemon, mandarin, clementine or grapefruit crop.

10. A method according to claim 9, wherein 5-amino-3-cyano-1-(2,6-dichloro-4-trifluoromethyl)phenyl-4-trifluoromethylsulfinylpyrazole is applied to the leaves.

11. A method according to claim 10, wherein 5-amino-3-cyano-1-(2,6-dichloro-4-trifluoromethyl)phenyl-4-trifluoromethylsulfinylpyrazole is applied at a rate of from about 25 to about 400 g/ha.

12. A method according to claim 10, wherein 5-amino-3-cyano-1-(2,6-dichloro-4-trifluoromethyl)phenyl-4-trifluoromethylsulfinylpyrazole is applied at a rate of from about 50 to about 100 g/ha.

13. A method according to claim 9, wherein 5-amino-3-cyano-1-(2,6-dichloro-4-trifluoromethyl)phenyl-4-trifluoromethylsulfinylpyrazole is applied at a rate of from about 25 to about 400 g/ha.

14. A method according to claim 9, wherein 5-amino-3-cyano-1-(2,6-dichloro-4-trifluoromethyl)phenyl-4-trifluoromethylsulfinylpyrazole is applied at a rate of from about 50 to about 100 g/ha.

15. A method according to claim 7, wherein 5-amino-3-cyano-1-(2,6-dichloro-4-trifluoromethyl)phenyl-4-trifluoromethylsulfinylpyrazole is applied to the leaves.

16. A method according to claim 15, wherein 5-amino-3-cyano-1-(2,6-dichloro-4-trifluoromethyl)phenyl-4-trifluoromethylsulfinylpyrazole is applied at a rate of from about 25 to about 400 g/ha.

17. A method according to claim 3, wherein 5-amino-3-cyano-1-(2,6-dichloro-4-trifluoromethyl)phenyl-4-trifluoromethylsulfinylpyrazole is applied at a rate of from about 50 to about 100 g/ha.

18. A method according to claim 7, wherein 5-amino-3-cyano-1-(2,6-dichloro-4-trifluoromethyl)phenyl-4-trifluoromethylsulfinylpyrazole is applied at a rate of from about 25 to about 400 g/ha.

19. A method according to claim 7, wherein 5-amino-3-cyano-1-(2,6-dichloro-4-trifluoromethyl)phenyl-4-trifluoromethylsulfinylpyrazole is applied at a rate of from about 50 to about 100 g/ha.

20. A method for treating a citrus plant attacked by greenfly of the Toxoptera genus, said method comprising applying to said citrus plant or to the medium in which it grows, in an amount effective to kill said greenfly, the compound 5-amino-3-cyano-1-(2,6-dichloro-4-trifluoromethyl)phenyl-4-trifluoromethylsulfinylpyrazole.

* * * * *